United States Patent
Geistlich et al.

(10) Patent No.: US 6,752,834 B2
(45) Date of Patent: *Jun. 22, 2004

(54) MEMBRANE FOR IN GUIDED TISSUE REGENERATION

(75) Inventors: Peter Geistlich, Stanstaad (CH); Zdenek Eckmayer, Weinheim (DE); Lothar Schlösser, Darmstadt (DE)

(73) Assignee: Ed Geistlich Soehne AG Fuer Chemische Industrie (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/545,465

(22) Filed: Apr. 7, 2000

(65) Prior Publication Data

US 2002/0177903 A1 Nov. 28, 2002

Related U.S. Application Data

(63) Continuation of application No. PCT/GB98/02976, filed on Oct. 5, 1998.

(30) Foreign Application Priority Data

Oct. 10, 1997 (GB) .............................................. 9721585

(51) Int. Cl.$^7$ .................................................. A61F 2/02
(52) U.S. Cl. ................................ 623/23.63; 623/23.75; 514/801
(58) Field of Search .............................. 623/1.47, 23.61, 623/23.74, 23.75, 23.63, 917, 23.71; 602/50; 424/423; 160/160, 1; 514/773, 801

(56) References Cited

U.S. PATENT DOCUMENTS

| 4,488,911 | A | * | 12/1984 | Luck et al. .................. 106/161 |
| 5,413,597 | A | * | 5/1995 | Krajicek .................... 623/1.47 |
| 5,567,806 | A |   | 10/1996 | Abdul-Malak et al. |
| 6,153,292 | A | * | 11/2000 | Bell et al. ................. 623/23.75 |
| 6,221,109 | B1 | * | 4/2001 | Geistlich et al. ......... 623/23.74 |

FOREIGN PATENT DOCUMENTS

| CA | 2248327 | 9/1997 |
| DE | 19654884 | 9/1997 |
| FR | 2679778 | 2/1993 |
| WO | 9013302 | 11/1990 |
| WO | 9518638 | 7/1995 |
| WO | 9624310 | 8/1996 |
| WO | 9625961 | 8/1996 |
| WO | 9732616 | 9/1997 |

OTHER PUBLICATIONS

D. Mutter et al., "Biomaterial supports for colonic wall defect healing," *Biomaterials* 17:1411–1415 (1996).
International Search Report, dated Mar. 22, 1999.

* cited by examiner

Primary Examiner—Brian E Pellegrino
(74) Attorney, Agent, or Firm—Rothwell, Figg, Ernst & Manbeck, PC

(57) ABSTRACT

The invention provides a multi-layer membrane comprising a matrix layer predominantly of collagen II and having an open sponge-like texture, and at least one barrier layer having a close, relatively impermeable texture. Such a membrane is particularly suitable for use in guided tissue regeneration, in particular for use in vivo in the reconstruction of bone or cartilage tissue.

19 Claims, No Drawings

MEMBRANE FOR IN GUIDED TISSUE REGENERATION

This application is a continuation-in-part of PCT international application No. PCT/GB98/02976 which has an international filing date of Oct. 5, 1998, which designated the United States, the entire contents of which are hereby incorporated by reference.

The present invention concerns a collagen membrane implant for use in guided tissue regeneration, in particular for use in vivo in the reconstruction of bone or cartilage tissue.

In tissue regeneration, it has long proved difficult to reconstruct cartilage tissue, such as in cartilage lesions. Cartilage injuries can occur in any joint though the larger joints, such as the knee and ankle, are most at risk. Such injuries can result from trauma, from degenerative conditions or osteochondritis dissecans. Cartilage injuries are a principal pathomechanical factor in the development of arthrosis. The liberation of enzymes leads to an inflammatory process of the synovia which in turn leads to abrasion of the cartilage and destruction of the joint surface. Recent attempts to regenerate articular cartilage in chondral defects in vivo include implantation of cultured autogenic articular chondrocytes (CACs). However, this technique has had limited success.

It is now generally accepted that reconstruction of tissue requires the provision of a matrix to serve as a guide for cells, which grow along and between the fibres of the matrix. More recently, the use of CACs seeded in both synthetic and natural resorbable matrices has been proposed. However, attempts to reconstruct cartilage tissue using matrices based on polylactic acid, polyglycolic acid and collagen I or III, have required the matrices to be loaded in vitro with chondrocytes prior to implantation. This gives rise to complications in terms of the sterile culture of the chondrocytes i.e. immunological inflammatory reactions by giant cells and fibroblastic cells at the interface between implants and tissue.

WO-A-96/25961 proposes a matrix implant based on collagen II which can be implanted at the in vivo site and which relies on the growth of native chondrocytes on the surface of the matrix to effect cartilage regeneration. The ability of such a matrix to effect complete regeneration of cartilage tissue is, however, limited.

There is thus a need for a matrix implant which will permit successful ingrowth of native chondrocytes and thus regeneration of cartilage tissue following implantation in vivo. We have now found that cartilage, and ultimately new bone tissue, can be reconstructed by the use of a collagen II matrix which in vivo is shielded not only from the surrounding connective tissue but also from the underlying bone or cartilage defect. It is envisaged that this may be achieved through the use of a multi-layer membrane implant which itself is capable of preventing the undesired ingrowth of any surrounding tissues into the matrix, or which may be surgically implanted at the site of the defect so as to achieve this effect.

Viewed from one aspect the invention thus provides a multi-layer membrane comprising a matrix layer predominantly of collagen II and having an open sponge-like texture, and at least one barrier layer having a close, relatively impermeable texture.

A particular advantage of the membrane according to the invention when used is that native cells are unable to penetrate or grow into the layer having a close, relatively impermeable texture.

Whilst not wishing to be bound by theory, it is now believed that successful cartilage regeneration requires that the rapid ingrowth not only of native tissue cells, such as connective tissues, blood vessels etc., but also of any new bone tissue into the site of the defect be prevented. This may be achieved using a double-layer membrane in accordance with the invention which serves to shield the collagen matrix from the ingrowth of native tissue cells from one side. During surgical implantation this may be used in combination with a tissue graft, e.g. a periosteal graft, effective to prevent the ingrowth of native tissue cells from the opposing side. Thus, for example, a periosteal graft may initially be sutured in place such that this provides a covering over the bone or cartilage defect. A double-layer membrane of the invention may then be implanted at the site of the defect such that this lies in contact with the graft and may be arranged in such a way that the matrix layer faces towards the bone defect. More preferably, a double-layer membrane of the invention is initially implanted at the site of the defect with the barrier layer facing towards the bone or cartilage defect. A periosteal graft is then arranged such that this lies in contact with the matrix layer. The graft may be adhered with a biocompatible adhesive such as fibrin glue, or pinned with resorbable polylactic pins, or if necessary or possible sutured in such a way that this then serves to provide an impermeable barrier to the ingrowth of any surrounding connective tissue.

In an alternative embodiment of the invention, the membrane itself may be effective to prevent the ingrowth of any native tissue cells. Thus, viewed from a further aspect the invention provides a membrane comprising at least three layers in which a matrix layer being predominantly made from collagen II and having an open sponge-like texture is provided between two barrier layers having a close, relatively impermeable texture.

The matrix layer is capable of acting as a medium for the ingrowth of native chondrocytes thereby effecting regeneration of cartilage tissue. However, to further aid in regenerating cartilage tissue the matrix layer may be impregnated with chondrocytes either prior to or following implantation in vivo. Whilst the matrix layer may be impregnated with chondrocytes immediately prior to implantation, e.g. by injection, it is expected that in general the chondrocytes will be introduced into the matrix layer by direct injection of a suspension of chondrocytes following implantation. In this way, chondrocytes present in the matrix layer of the membrane are able to effect regeneration of cartilage, and ultimately new bone, whilst the membrane at the same time prevents the ingrowth of other cell types from the surrounding tissues.

Chondrocytes for use in the invention may be obtained from cell sources which include allogenic or autogenic cells isolated from articular cartilage, periosteum and perichondrium, and mesenchymal (stromal) stem cells from bone marrow. Since allogenic cells carry the potential for immune response and infectious complications, it is preferable to isolate the chondrocytes from autogenic cells, especially from autogenic articular cartilage. Techniques for harvesting cells are known and include enzymatic digestion or outgrowth culture. The harvested cells are then expanded in cell culture prior to reintroduction to the body. In general, at least $10^6$, preferably at least $10^7$ cells should be impregnated into the matrix layer to provide for optimal regeneration of cartilage tissue.

In general, it is desirable for the matrix layer of the membrane according to the invention to contain glycosaminoglycans (GAGs) such as hyaluronic acid, chondroitin 6-sulphate, keratin sulphate, dermatan sulphate etc. which serve to provide a natural medium in which chondrocytes can become embedded and grow. Whilst it is possible to incorporate into the collagen matrix glycosaminoglycans from different sources which do not necessarily have the same composition, molecular weight and physiological properties as those from cartilage, preferred glycosaminoglycans are those extracted from cartilage itself. In general, the matrix layer preferably contains from 1 to 10 wt % of glycosaminoglycans, for example 2 to 6 wt %. Although some glycosaminoglycans may be present in the impermeable layer, the greater part will be present in the matrix layer.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix layer is thus substantially free from any proteoglycans. Conveniently, this may be achieved by preparing the matrix layer from a mixture of a purified telopeptide-free collagen II material and glycosaminoglycans.

Other additives which may also be present in the matrix layer include, for example, chondronectin, laminin, fibronectin, calcium alginate or anchorin II to assist attachment of the chondrocytes to the collagen II fibres, and growth factors such as cartilage inducing factor (CIF), insulin-like growth factor (IGF), transforming growth factor β (TGFβ) present as homodimers or heterodimers and bone morphogenetic factors (BMP) such as native or recombinant human BMP-2, BMP-3 (osteogenin), BMP-4 and BMP-7 (OP-1, osteogenetic protein-1). BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralised bone matrix consist of 90% collagen and 10% non-collagenous proteins (NCP) for BMP activity or for BMP/NCP induced chondrogenesis. Bone matrix-insoluble collagenous matrix and laminin or fibronectin act as carriers for BMPs. Some growth factors may also be present in the impermeable layer. However, the greater part will be present in the matrix layer. In general, the membrane contains from 100 µg to 5 mg of growth factors.

As indicated above, the membrane comprises at least two layers having different structures. Preferably, the barrier layer of the membrane is predominantly made from collagen I and III. Alternatively, this may comprise a synthetic material, e.g. a synthetic resorbable polymer network optionally coated with a collagen material such as type I and/or type III collagen.

Examples of suitable synthetic materials include polyesters, polyglycolic and polylactic acids (PLA) homopolymers and copolymers, glycolide and lactide copolymers, polyorthoesters and polycaprolactones. Many examples of these are openly available, e.g. from Boehringer Ingelheim in their RESOMER range. PLA polymers as wax with an appropriate molecular size of ca. 650–1200 and not too rapid a degradation are preferred. A particularly preferred biodegradable polymer is poly(D,L-lactic acid) in which the ratio of D-lactide to L-lactide is approx. 70:30. An advantage of such synthetic materials is that these can have high mechanical stability which allows the membrane implant to be stretched over complex, three dimensional bone defects without tearing. Such materials are also suitable for suturing.

Advantageously, the barrier layer consists of long collagen fibres which are so closely connected that high molecular substances cannot permeate this barrier. The long fibres provide high tensile strength and resistance to tearing so that the material is not only a good separation membrane but can also be readily sewn. It is important in surgery that membrane implants can be sewn or pinned into position and many of the membranes which have previously been proposed do not provide this capability. The membrane in accordance with the invention is mechanically stable enough to be handled surgically for implantation.

The matrix layer is very porous and may have a specific weight as low as 0.02, which permits cells very rapidly to grow into this layer. This layer of the membrane, which normally also contains glycosaminoglycans, swells strongly and can take up as much as 5000% of liquid. Ideally, the matrix layer should provide a pore structure (pore volume fraction and pore size) which allows cell adhesion and growth and which permits the seeded cells to maintain the chondrocytic phenotype, characterised by synthesis of cartilage-specific proteins. Pore sizes will depend on the freeze drying process used to produce the collagen II matrix but can be expected to be in the range of from 10 to 120 µm, e.g. 20 to 100 µm. Optionally the pore size should be around 85 µm. Such a pore size may readily be obtained by slow freezing at from −5 to −10° C. for about 24 hours followed by freeze-drying, or by adding ammonium bicarbonate to the slurry before lyophilisation.

The matrix layer of the membrane is preferably provided by collagen II material obtained from cartilage, preferably hyaline cartilage from pigs.

Whilst the desired thickness of the matrix layer will depend upon the nature of the bone or chondral defect to be treated, in general this can be expected to be in the range of from 2 to 10 mm, e.g. from 4 to 6 mm. The thickness of the barrier layer is preferably from 0.2 to 2 mm, e.g. from 0.2 to 0.7 mm.

The barrier layer may be provided by a natural animal membrane comprising collagen I and III. Being derived from a natural source, this is totally resorbable in the body and does not form toxic degradation products. Such membranes also have particularly high tear strength in either a wet or dry state and can therefore be surgically stitched if necessary. When moist the material is very elastic which allows this to be stretched over irregularly shaped bone defects.

Besides collagen, natural animal membranes contain many other biomaterials, which must be removed. It is known to treat such membranes with enzymes, solvents or other chemicals to effect purification and to use these membranes in medicine. Most of these materials are too thin and very often not particularly easy to use. The collagen fibrils have lost their native character and further disadvantages are that the material often has insufficient strength for use as a sewable material, has no water-swelling properties and provides no difference between the smooth grain side and the fibrous flesh side. The fibrous form of purified telopeptide-free collagen Type I or II, being less soluble and biodegradable, has been found to provide the most advantageous carrier material.

Membranes providing the barrier layer of the product according to the invention include peritoneum membrane from calves or pigs which retain their natural collagen structure. Peritoneum membranes from young pigs aged 6–7 weeks old (weighing 60–80 kg) are especially preferred.

The barrier layer should preferably comprise pure, native (not denatured) insoluble collagen and may be prepared in accordance with the method described in WO-A-95/18638. The natural membrane may thus first be treated with alkali, for example aqueous NaOH at a concentration of from 0.2–4% by weight. This serves to saponify any fats and also proteins which are sensitive to alkali. The second step is the treatment of the material with an acid, usually an inorganic acid such as HCl. This eliminates acid-sensitive contaminants. The material is subsequently washed until the pH is in the range 2.5–3.5. The membrane then has a smooth or grain side and a looser more fibrous side. It may be beneficial to effect some cross-linking of the membrane by heating to 100–120° C.

The collagen II material used to provide the matrix layer of the membrane can be obtained from cartilage by a similar procedure to that described above in relation to the barrier layer comprising predominantly collagen I and III. It is preferable to remove water from the cartilage by treatment with acetone followed by extraction of fat with a hydrocarbon solvent such as n-hexane, though alkanols such as ethanol, ethers such as diethyl ether or chlorinated hydrocarbons such as chloroform, or mixtures thereof may be used. The defatted material is then subjected to treatment with alkali which saponifies any residual fat and degrades some of the proteins present. Finally, the material is treated with acid which effects further protein degradation. The material is allowed to swell in water and is passed through a colloid mill to produce a slurry.

To produce the multi-layer membrane, the soft slurry containing collagen II is applied to the fibrous side of the smooth membrane prepared, for example in accordance with WO-A-95/18638. Normally, the membrane will be placed on a smooth surface with the grain side down so that the collagen II slurry can readily be applied, e.g. by rubbing into the fibrous side of the membrane. The slurry thus forms a layer of any desired thickness which firmly adheres to the collagen membrane. The double-layer so formed is then subjected to freezing and freeze-drying to provide the desired sponge-like structure having a desired pore size. If necessary, some of the matrix layer may be removed to provide a double-membrane of uniform thickness. To produce a three-layer membrane, a second smooth membrane is then placed on top of the matrix layer with its fibrous side in contact with the matrix layer.

The collagen II slurry to be applied to the membrane in general contains 1.0–4.0 weight % of the collagen, advantageously 2–3 weight %. Conveniently, the pH value of this mixture should be adjusted to 2.5–4.5, advantageously 3.0–4.0.

Advantageously, the collagen II material may be cross-linked after the freeze-drying step to stabilise the matrix layer. This also serves to increase the mechanical stability of the matrix layer and to reduce its rate of resorption by the body. Ideally, the degree of cross-linking should be such that the rate of degradation of the matrix matches the rate of tissue regeneration. Physically, cross-linking may be carried out by heating, but this must be effected carefully to avoid undesired loss of resorbability. Heating to temperatures of 100–120° C. for a period of from 30 minutes to 5 hours is preferable. More preferably, cross-linking may be effected by UV irradiation using a UV lamp e.g. for a period of up to 8 hours.

The collagen II material advantageously contains glycosaminoglycans. The latter actually reacts with the collagen II to effect some cross-linking and produces an insoluble product. If necessary, further cross-linking can be effected by heating the material or by UV irradiation as discussed above. The reaction between the glycosaminoglycans and the collagen can be effected at ambient temperatures at a pH in the range 2.5–3.5. The quantity of glycosaminoglycan may be between 1 and 10% by weight. The material may be subjected to freezing and freeze-drying immediately after such treatment.

Alternatively, slurry formation may be effected by raising the pH of the collagen II mass. In this procedure, the mass is cooled to about 4° C. and the pH value slowly raised by addition of cold aqueous NaOH at 4° C. up to a pH value 6.5–7.5. Subsequently, the mass is held at ambient temperature for 15–25 hours. In this time, the slurry is formed and after slurry formation, the mass can be frozen and freeze-dried.

A still further alternative is to neutralise the collagen II mass to a pH value 6.8–7.4, subsequent to removal of air. The mixture is placed in the mould and incubated for 15–20 hours at 37° C. A fine slurry develops which can subsequently be frozen and freeze-dried.

Which of the above three methods is used depends upon the properties of the desired product. The first process gives the most stable product. However, the precipitation may give clumps of material and must be very carefully carried out. The second method gives a soft and uniform product which is, however, more soluble than the product of the first process.

In the production of the slurry, it is possible to additionally introduce further desirable substances such as medicines, e.g. antibacterials such as taurolidine or antibiotics such as gentamycin.

After the application of the slurry to the membrane, the material is frozen. In order to obtain a reproducible pore size, the freezing must be carefully controlled and the rate and time of freezing, the pH value and the particle size must be accurately controlled. In order to obtain very small pores, the material may be shock frozen at very low temperature.

The frozen membrane is then freeze-dried and subsequently heated to 110–130° C. In this way, some cross-linking is effected. Subsequently, the freeze-dried biomembrane may be adjusted to the required thickness so that the thickness of the matrix layer is commonly about 2 mm. The double membrane is then sterilised, for example by gamma-irradiation or with ethyleneoxide. Sterilisation by strong irradiation e.g. with $^{60}$Co in doses of 25 kGy may deactivate the BMPs. In such circumstances, the sterile matrix may be impregnated with BMPs in sterile saline prior to implantation.

The membrane according to the invention can be used in medicine in the following ways:

As a material for guided tissue regeneration. Cell growth is encouraged by the matrix layer. The barrier layer inhibits undesired cell growth.

As a material for the repair of chondral defects, i.e. lesions which do not penetrate the subchondral plate, and in the repair of osteochondral defects.

The invention also provides the use of a multi-layer collagen membrane as described above in guided tissue regeneration. The collagen II content of the membrane is particularly suitable for regeneration of cartilage tissue but is also suitable for other tissue types.

Viewed from a further aspect the invention thus provides a membrane as hereinbefore described for use as a guided tissue regeneration implant.

The invention further provides a method of treating a bone or cartilage defect in the human or non-human animal body, said method comprising application of a membrane as hereinbefore described to the defect, said membrane being oriented such that the barrier layer prevents the ingrowth of undesirable tissue types into the area of bone or cartilage regeneration the membrane can be applied during conventional open surgery, or during arthroscopic surgery.

The following examples are given by way of illustration only. In the Examples, all steps have to be performed under aseptic conditions in, for example, Clean Rooms.

EXAMPLE 1

(A) Peritoneal membranes from young calves are completely freed from flesh and grease by mechanical means, washed under running water and treated with 2% NaOH solution for twelve hours. The membranes are then washed under running water and acidified with 0.5% HCl. After the material has been acidified through its entire thickness (about three hours) the material is washed until a pH of 3.5 is obtained. The material is then shrunk with 7% saline solution, neutralised with 1% $NaHCO_3$ solution and washed under running water. The material is then dehydrated with acetone and degreased with n-hexane.

(B) Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optical particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9–11. The dissolved impurities were washed out and separated from the cartilage. The liquid resulting from the alkaline treatment was collected for the recovery of glycosaminoglycan.

The collagen material was then treated with strong HCl (about 3% by weight) initially at a pH value under 1.0. The treatment time was 4–6 hours.

Subsequently, the material was washed with cold water long enough for the pH value to rise to 3–3.5. All impurities were removed and the product was a salt-free collagen mass, suitable for production of a sponge or other collagen material. For that purpose, the cartilage mass may be, according to the intended result, degassed, frozen and freeze-dried.

The extract resulting from alkaline treatment above contained glycosaminoglycan, alkali, denatured proteins and salts. The extract was firstly neutralised with HCl, the pH value after neutralisation being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10,000 daltons. In this way, salts were removed to leave purified glycosaminoglycan.

The glycosaminoglycan solution so obtained was admixed with collagen material from above to provide a collagen II matrix containing glycosaminoglycan.

The collagen II mass had the following properties:

| | |
|---|---|
| TG = | 2.8 weight % |
| GAG = | 3 weight % (calculated on the basis of collagen) |
| pH value | 3.5 |

(C) The freshly prepared peritoneum membrane prepared as in (A) above was uniformly soaked in water and laid flat on a glass plate with the fibrous side upwards. Subsequently, the membrane was thoroughly wetted with the collagen II mass prepared as in (B) above. The membrane was stretched flat in all directions so as to remain adhered to the plate. The collagen II mass was thereby rubbed into the membrane.

The very thick mass was applied to the membrane and the plate was left overnight in the refrigerator at a temperature of about 4° C. In that period a slurry was formed.

The slurry was frozen under the following conditions:

| | |
|---|---|
| Temperature of the bath = | −12° C. |
| Time = | 40 minutes |

Subsequently, the frozen slurry was freeze-dried and then warmed to 125° C.

Freeze-drying time=14 hours.

The collagen II matrix layer was subsequently split to a thickness of 1 mm.

EXAMPLE 2

The freshly prepared peritoneum membrane from Example 1(A) was applied to a glass plate and the thick collagen II mass, having the properties as in Example 1, was rubbed into the membrane. 50 g of the collagen II mass was diluted to 100 ml with distilled water and thoroughly stirred. During the stirring, 100 ml of glycosaminoglycan solution was slowly added. Collagen was precipitated in the form of a mass together with GAG. After the precipitation, the mass was homogenised ahd the dispersion so obtained was applied to the membrane. A slurry formed overnight and the treated membrane was further processed as described in Example 1.

What is claimed is:

1. A membrane comprising a resorbable multi-layer membrane for use in vivo in the reconstruction of bone or cartilage tissue at a site of a defect in said tissue, said resorbable multi-layer membrane comprising a matrix layer for facing toward said defect, the matrix layer having a matrix consisting essentially of collagen II and having an open sponge-like texture, and at least one barrier layer for facing away from said defect so as to prevent ingrowth of undesirable tissue types into said defect, the barrier layer having a close, relatively impermeable texture, the at least one barrier layer consisting essentially of a barrier layer material selected from the group consisting of collagen I, collagen III and a mixture thereof, wherein said multi-layer membrane is formed by application of said matrix layer to said at least one barrier layer as a slurry, so that said matrix layer is adhered firmly to and in direct contact with said at least one barrier layer, wherein firm adherence of the matrix layer to said at least one barrier layer results essentially solely from application of said slurry to said at least one barrier layer.

2. A membrane as claimed in claim 1 comprising a single barrier layer.

3. A membrane as claimed in claim 1 in which the matrix layer is provided between two barrier layers.

4. A membrane as claimed in claim 1 in which the matrix layer is provided by collagen II material derived from natural cartilage.

5. A membrane as claimed in claim 4 wherein the collagen II material is derived from hyaline cartilage from pigs.

6. A membrane as claimed in claim 4 in which the collagen II material is physically cross-linked.

7. A membrane as claimed in claim 5 in which the at least one barrier layer is derived from peritoneum membrane from calves or pigs.

8. A membrane as claimed in claim 1, in which the matrix layer is impregnated with chondrocytes isolated from articular cartilage, periosteum, periocardium or mesenchymal stem cells from bone marrow.

9. A membrane as claimed in claim 1 in which the matrix layer, said at least one barrier layer, or each said layer is impregnated with a glycosaminoglycan.

10. A membrane as claimed in claim 9 wherein the glycosaminoglycan is hyaluronic acid, chondroitin 6-sulphate, keratin sulphate or dermatan sulphate.

11. A membrane as claimed in claim 1 in which the matrix and barrier layers are substantially free from proteoglycans.

12. A membrane as claimed in claim 1 in which the matrix layer, said at least one barrier layer, or each of the layers further comprise chondronectin, lectin, fibronectin, calcium alginate, anchorin II, growth factors or bone morphogenetic factors.

13. A membrane as claimed in claim 12 wherein the growth factors are cartilage inducing factor (CTF), insulin-like growth factor (IGF), or transforming growth factor (TGF).

14. A membrane as claimed in claim 12 wherein the bone morphogenetic factors are human BMP-2, BMP-3, BMP-4 or BMP-7.

15. A process for the preparation of a membrane as claimed in claim 1 in which a collagen II slurry is applied to a surface of a barrier membrane having a close, relatively impermeable texture, followed by freeze-drying whereby to provide a matrix layer having an open sponge-like structure.

16. A method of treating a bone or cartilage defect in the human or non-human animal body, said method comprising application of a membrane as claimed in claim 1 to the defect, said membrane being oriented such that the barrier layer or layers prevent the ingrowth of undesirable tissue types into the area of bone or cartilage regeneration.

17. The method of claim 16 wherein said membrane is applied during arthroscopic surgery.

18. A method of treating a bone or cartilage defect in the human or non-human animal body, said method comprising application of a membrane as claimed in claim 1 to the defect, said membrane being oriented such that the barrier layer or layers prevent the ingrowth of undesirable tissue types into the area of bone or cartilage regeneration, and wherein the matrix layer of said membrane is impregnated with chondrocytes either immediately prior to or following application to the defect.

19. The method of claim 18 wherein said membrane is applied during arthroscopic surgery.

* * * * *